(12) United States Patent
Suzuki et al.

(10) Patent No.: US 7,700,802 B2
(45) Date of Patent: Apr. 20, 2010

(54) METHOD OF SEPARATING STEREOISOMERS OF DICARBOXYLIC ACID HAVING NORBORNENE OR NORBORNANE STRUCTURE, OR DERIVATIVE THEREOF

(75) Inventors: Toru Suzuki, Kokubunji (JP); Tetsuo Yamanaka, Ichihara (JP)

(73) Assignee: Hitachi Chemical Co., Ltd., Tokyo (JP)

( * ) Notice: Subject to any disclaimer, the term of this patent is extended or adjusted under 35 U.S.C. 154(b) by 613 days.

(21) Appl. No.: 10/595,134

(22) PCT Filed: Sep. 3, 2004

(86) PCT No.: PCT/JP2004/012843

§ 371 (c)(1),
(2), (4) Date: Jan. 16, 2007

(87) PCT Pub. No.: WO2005/023746

PCT Pub. Date: Mar. 17, 2005

(65) Prior Publication Data

US 2007/0142668 A1    Jun. 21, 2007

(30) Foreign Application Priority Data

Sep. 3, 2003    (JP)    ............... 2003-311121

(51) Int. Cl.
*C07B 57/00*    (2006.01)
*C07C 61/12*    (2006.01)
*C07D 307/94*    (2006.01)
(52) U.S. Cl. .................. 562/401; 562/502; 549/237
(58) Field of Classification Search ................ 562/466, 562/401, 502; 549/237
See application file for complete search history.

(56) References Cited

U.S. PATENT DOCUMENTS 6,465,551 B1 * 10/2002 Zhao et al. .................. 524/284

FOREIGN PATENT DOCUMENTS

| FR | 2.097.667 | 3/1972 |
| JP | 63-057589 | 3/1988 |
| JP | 11-305444 | 11/1999 |
| JP | 2002-030115 | 1/2002 |
| JP | 2002-088120 | 3/2002 |
| JP | 2002-284812 | 10/2002 |
| WO | 02/077092 | 10/2002 |

OTHER PUBLICATIONS

Pincock, Richard E., et al. "Thermal Isomerization in Polycrystalline exo- and endo-5-Norbornene-2,3-dicarboxylic Anhydrides," Journal of the American Chemical Society, Dec. 20, 1967, pp. 6890-6897.
Asrar, Jawed, "Metathesis Polymerization of N-Phenylnorbornenedicarboximide," Macromolecules, 1992, pp. 5150-5156, vol. 25, No. 20.
Journal of the American Chemical Society, Jan. 5, 1963, pp. 115-116.
Pandey, Bipin et al, "A Remarkably Efficient Photochemical Methodology for Endo to Exo Isomerization of Diels-Alder Cycloadducts," Chemistry Letters, 1991, pp. 1173-1176.
Stager, Geza, et al. "Regioselective Synthesis of 3-endo-Hydroxymethyl-5-exo-phenylbiclo[2.2.1]heptan-2-endo-amine and its Transformation into Saturated or Partially Saturated Di-endo-fused Hetercycles," Acta Chemica Scandinavica, 1996, pp. 922-930, vol. 50.
International Search Report issued in corresponding application No. PCT/JP2004/012843, completed Nov. 15, 2004 and mailed Dec. 7, 2004.
Supplementary European Search Report issued in corresponding application No. 04772792.0, completed Oct. 23, 2006 and mailed Oct. 30, 2006.
First Official Action issued on Nov. 9, 2007 in the corresponding Chinese application No. 200480025321.1 with English Translation thereof (3 sheets).

(Continued)

*Primary Examiner*—Taylor Victor Oh
(74) *Attorney, Agent, or Firm*—Griffin & Szipl, P.C.

(57) ABSTRACT

A method of efficiently extracting a high-purity stereoisomer from a mixture comprising the endo isomer and the exo isomer of a dicarboxylic acid having a norbornene or norbornane structure, or a derivative thereof. The present invention relates to a method of separating the endo isomer and the exo isomer of a dicarboxylic acid represented by a general formula (1) or (2) or a derivative thereof, and includes the step of stirring and mixing a mixture comprising mainly the endo isomer of the dicarboxylic acid represented by the general formula (1) or (2) or a derivative thereof, and the exo isomer of the dicarboxylic acid represented by the general formula (1) or (2) or a derivative thereof, with a basic compound and a solvent.

[Formula 1]

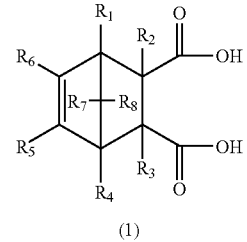

(1)

(wherein, $R_1$ to $R_8$ represent a hydrogen atom, methyl group, ethyl group, or butyl group),

[Formula 2]

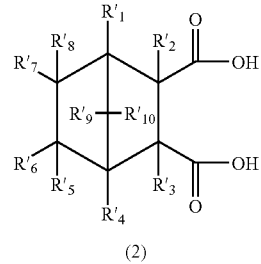

(2)

(wherein, $R'_1$ to $R'_{10}$ represent a hydrogen atom, methyl group, ethyl group, or butyl group).

17 Claims, No Drawings

OTHER PUBLICATIONS

Notification of First Examination Opinion (Main Text), Application No. 2004/00253211, one page.

Chemica Scandinavica, 1996: 50 922-930, Chem. Lett., 1991:(7):1173-1176, (3 sheets).

* cited by examiner

METHOD OF SEPARATING STEREOISOMERS OF DICARBOXYLIC ACID HAVING NORBORNENE OR NORBORNANE STRUCTURE, OR DERIVATIVE THEREOF

This is a National Phase Application in the United States of International Patent Application No. PCT/JP2004/012843 filed Sep. 3, 2004, which claims priority on Japanese Patent Application No. 2003-311121, filed Sep. 3, 2003. The entire disclosures of the above patent applications are hereby incorporated by reference.

TECHNICAL FIELD

The present invention relates to a method of separating the endo isomer and the exo isomer of a dicarboxylic acid having a norbornene or norbornane structure, or a derivative thereof.

Furthermore, the present invention also relates to a method of separating the endo isomer and the exo isomer of a salt of a dicarboxylic acid having a norbornene or norbornane structure.

In addition, the present invention also relates to an endo isomer or exo isomer of a dicarboxylic acid having a norbornene or norbornane structure, or a derivative thereof, which has been refined to a high degree of purity using the above method.

BACKGROUND ART

Dicarboxylic acids or dicarboxylic anhydrides having a norbornene or norbornane structure are useful as the raw materials for agricultural chemicals or as industrial raw materials. Dicarboxylic acids or dicarboxylic anhydrides having a norbornene or norbornane structure are known to exist as stereoisomers, which include an endo isomer and an exo isomer with different melting points and reactivity.

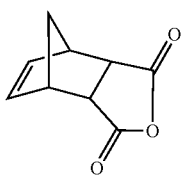

5-norbornene-endo-2,3-dicarboxylic anhydride [Formula 1]

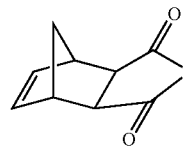

5-norbornene-exo-2,3-dicarboxylic anhydride [Formula 2]

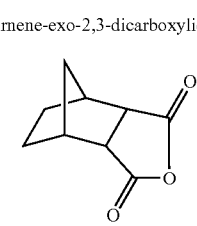

norbornane-endo-2,3-dicarboxylic anhydride [Formula 3]

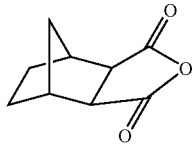

norbornane-exo-2,3-dicarboxylic anhydride [Formula 4]

Dicarboxylic anhydrides having a norbornane structure such as 5-norbornene-2,3-dicarboxylic anhydride can be reacted with an amine compound and then subjected to a ring-opening polymerization to yield an imide compound with a high glass transition point and a low dielectric constant that is useful as an electronic material, but it is known that the polymer reactivity and the physical properties of the product polymer differ depending on the steric structure of 5-norbornene-2,3-dicarboxylic anhydride (for example, see Macromolecules, (U.S.), 25 (1992), p. 5150). Furthermore, it is also known that when a low dielectric constant polymer is obtained by an addition polymerization at the olefin portion of an imide derivative of 5-norbornene-2,3-dicarboxylic acid, the exo isomer exhibits superior reactivity to the endo isomer (for example, see Japanese Laid-Open Publication No. 2002-30115, Japanese Laid-Open Publication No. 2002-88120, and Japanese Laid-Open Publication No. 2002-284812). In addition, the tetracarboxylic acid that is a derivative of the exo isomer is an important raw material for soluble polyimide acid (for example, see Japanese Laid-Open Publication No. Sho 63-57589). In this manner, the differences in reactivity and the like between the endo and exo isomers of 5-norbornene-2,3-dicarboxylic acid or the anhydride thereof mean that their respective levels of usability vary depending on the application.

Generally, this 5-norbornene-2,3-dicarboxylic acid or the anhydride thereof is prepared by a Diels-Alder reaction between maleic acid or maleic anhydride and cyclopentadiene, which yields a product containing the endo isomer as the primary component with a small quantity of the exo isomer.

Accordingly, in order to obtain 5-norbornene-exo-2,3-dicarboxylic acid or the anhydride thereof, the mixture obtained from the above Diels-Alder reaction, comprising the primary component 5-norbornene-endo-2,3-dicarboxylic acid or the anhydride thereof together with a small quantity of 5-norbornene-exo-2,3-dicarboxylic acid or the anhydride thereof, is usually heated, either alone or in combination with decalin or the like, thereby converting the endo isomer to the exo isomer via a thermal isomerization (for example, see The Journal of the American Chemical Society, (U.S.), 1963, pp. 115 to 116). However, at a temperature of 140° C. to 150° C., the endo and exo isomers of 5-norbornene-2,3-dicarboxylic acid or the anhydride thereof reach an equilibrium state in which the ratio of endo isomer/exo isomer is approximately 54/46, meaning the pure exo isomer cannot be obtained solely by thermal isomerization. Consequently, pure 5-norbornene-exo-2,3-dicarboxylic acid or the anhydride thereof is generally obtained by repeated recrystallizations (for example, see The Journal of the American Chemical Society, (U.S.), 1967, 69, p. 6896). However in order to obtain high-purity 5-norbornene-exo-2,3-dicarboxylic acid or the anhydride thereof using this recrystallization method, either the recrystallization is repeated a number of times, or a large quantity of solvent is used during the recrystallization, and as a result, a problem arises in that the yield of the 5-norbornene-exo-2,3-dicarboxylic acid or the anhydride thereof is very low. Furthermore, extracting the less prevalent stereoisomer efficiently and with a high degree of purity from a mixture of the endo isomer and the exo isomer is difficult.

Furthermore, a method in which 5-norbornene-exo-2,3-dicarboxylic acid is obtained experimentally by a photoisomerization reaction at 300 nm, using ethyl alcohol as a solvent and triethylamine as a catalyst, has also been reported (for example, see Chemistry Letters (Japan), 1991, pp. 1173 to 1176). However, because this method uses an amine and an alcohol, a problem arises in that a reaction occurs between the alcohol and the acid anhydride.

In addition, a dicarboxylic acid having a norbornane structure or the anhydride thereof is generally prepared by hydrogenation of the 5-norbornene-2,3-dicarboxylic acid or anhydride thereof obtained using the Diels-Alder reaction described above, and the product contains the endo isomer as the primary component with a small quantity of the exo isomer. Accordingly, in a similar manner to that descried above, for a dicarboxylic acid having a norbornane structure or the anhydride thereof, extracting the less prevalent stereoisomer efficiently and with a high degree of purity from a mixture of the endo isomer and the exo isomer is difficult.

DISCLOSURE OF INVENTION

The present invention resolves the problems described above, and has an object of providing a method of efficiently extracting a high-purity stereoisomer from a mixture comprising the endo isomer and the exo isomer of either a dicarboxylic acid having a norbornene or norbornane structure, or a derivative thereof.

Furthermore, the present invention also has an object of efficiently extracting a high-purity stereoisomer from a mixture comprising the endo isomer and the exo isomer of a salt of a dicarboxylic acid having a norbornene or norbornane structure.

Furthermore, another object of the present invention is to provide the endo isomer of a dicarboxylic acid having a norbornene or norbornane structure, or a derivative thereof, which has been separated with a high degree of purity.

In addition, yet another object of the present invention is to provide the exo isomer of a dicarboxylic acid having a norbornene or norbornane structure, or a derivative thereof, which has been separated with a high degree of purity.

As a result of intensive investigation, the inventors of the present invention discovered that by utilizing the difference in solubility between a neutralized salt of the endo isomer and a neutral salt of the exo isomer of a dicarboxylic acid having a norbornene or norbornane structure, one of the stereoisomers could be extracted efficiently and with a high degree of purity, and they were hence able to complete the present invention.

Accordingly, the present invention provides a method of separating the endo isomer and the exo isomer of a dicarboxylic acid represented by general formula (1) or (2), which are shown below, or a derivative thereof, comprising the step of stirring and mixing a mixture comprising mainly the endo isomer of the dicarboxylic acid represented by the general formula (1) or (2) or a derivative thereof, and the exo isomer of the dicarboxylic acid represented by the general formula (1) or (2) or a derivative thereof, with a basic compound and a solvent. Formula 5, which may also referred to as "general formula (1)," corresponds to

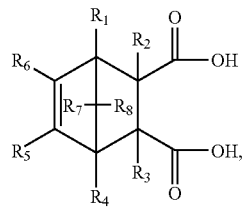

wherein, $R_1$ to $R_8$ represent a hydrogen atom, methyl group, ethyl group, or butyl group. Formula 6, which may also be referred to as "general formula (2)," corresponds to

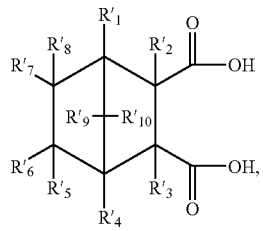

wherein, $R'_1$ to $R'_{10}$ represent a hydrogen atom, methyl group, ethyl group, or butyl group.

Preferably, the present invention provides a method of separating the endo isomer and the exo isomer of a dicarboxylic acid represented by the general formula (1) or a derivative thereof, comprising the step of stirring and mixing a mixture comprising mainly the endo isomer and the exo isomer of the dicarboxylic acid represented by the general formula (1) or a derivative thereof, with a basic compound and a solvent.

Furthermore, preferably, the present invention provides a method of separating the endo isomer and the exo isomer of a dicarboxylic acid represented by the general formula (2) or a derivative thereof, comprising the step of stirring and mixing a mixture comprising mainly the endo isomer and the exo isomer of the dicarboxylic acid represented by the general formula (2) or a derivative thereof, with a basic compound and a solvent.

Furthermore, another aspect of the present invention provides a method of separating the endo isomer and the exo isomer of a salt of a dicarboxylic acid represented by the general formula (1) or (2), comprising the step of stirring and mixing a mixture comprising mainly the endo isomer of the salt of the dicarboxylic acid represented by the general formula (1) or (2), and the exo isomer of the salt of the dicarboxylic acid represented by the general formula (1) or (2), with a solvent.

The endo isomer and the exo isomer of salts of the dicarboxylic acid correspond to either general formula (1),

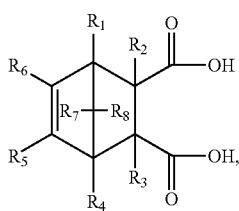

(1)

wherein, $R_1$ to $R_8$ represent a hydrogen atom, methyl group, ethyl group, or butyl group, or to general formula (2),

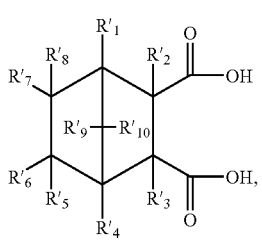

(2)

wherein, $R'_1$ to $R'_{10}$ represent a hydrogen atom, methyl group, ethyl group, or butyl group.

Preferably, this other aspect of the present invention provides a method of separating the endo isomer and the exo isomer of a salt of a dicarboxylic acid represented by the general formula (1), comprising the step of stirring and mixing a mixture comprising mainly the endo isomer and the exo isomer of the salt of the dicarboxylic acid represented by the general formula (1), with a solvent.

Furthermore, preferably, this another aspect of the present invention provides a method of separating the endo isomer and the exo isomer of a salt of a dicarboxylic acid represented by the general formula (2), comprising the step of stirring and mixing a mixture comprising mainly the endo isomer and the exo isomer of the salt of the dicarboxylic acid represented by the general formula (2), with a solvent.

Furthermore, the methods of separating the endo isomer and the exo isomer described above may also include the step of filtering the mixture obtained from the stirring and mixing step, and either obtaining the endo isomer of the salt of the dicarboxylic acid represented by the general formula (1) or (2) as the liquid phase, or obtaining the exo isomer of the salt of the dicarboxylic acid represented by the general formula (1) or (2) as the solid phase.

Furthermore, the methods of separating the endo isomer and the exo isomer described above may also include the step of obtaining the endo isomer or the exo isomer of the dicarboxylic acid represented by the general formula (1) or (2) from the endo isomer or the exo isomer of the salt of the dicarboxylic acid represented by the general formula (1) or (2).

Furthermore, the methods of separating the endo isomer and the exo isomer described above may also include the step of obtaining the endo isomer or the exo isomer of the anhydride of the dicarboxylic acid represented by the general formula (1) or (2) from the endo isomer or the exo isomer of the dicarboxylic acid represented by the general formula (1) or (2) or the salt thereof.

In addition, another aspect of the present invention provides the endo isomer of a dicarboxylic acid represented by the general formula (1) or (2) or a derivative thereof, obtained using the method described above.

In addition, yet another aspect of the present invention provides the exo isomer of a dicarboxylic acid represented by the general formula (1) or (2) or a derivative thereof, obtained using the method described above.

This Application is based upon and claims the benefit of priority from prior Japanese Application 2003-311121 filed on Sep. 3, 2003, the entire contents of which are incorporated by reference herein.

BEST MODE FOR CARRYING OUT THE INVENTION

A method of the present invention for separating the endo isomer and the exo isomer of a dicarboxylic acid represented by a general formula (1) or (2) or a derivative thereof, comprises the step of stirring and mixing a mixture (hereafter also referred to as the "mixture of the general formula (1) or (2) type") comprising mainly the endo isomer of the dicarboxylic acid represented by the general formula (1) or (2) or a derivative thereof (hereafter also referred to as the "endo isomer of the general formula (1) or (2) type"), and the exo isomer of the dicarboxylic acid represented by the general formula (1) or (2) or a derivative thereof (hereafter also referred to as the "exo isomer of the general formula (1) or (2) type"), with a basic compound and a solvent. Thus, a compound of general formula (1),

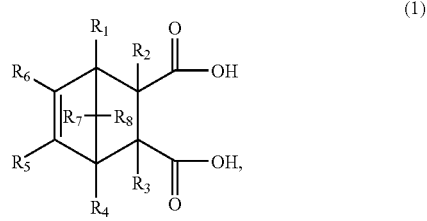

(1)

has an endo isomer form and an exo isomer form. In the general formula (1), $R_1$ to $R_8$ represent a hydrogen atom, methyl group, ethyl group, or butyl group. Compounds in which either $R_1$ to $R_8$ are all hydrogen atoms, or one of $R_1$ to $R_8$ is a methyl group, ethyl group or butyl group, and the remainder of $R_1$ to $R_8$ are hydrogen atoms are preferred. Likewise, a compound of general formula (2),

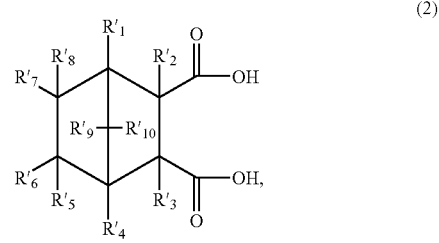

(2)

has an endo isomer form and an exo isomer form. In the general formula (2), $R'_1$ to $R'_{10}$ represent a hydrogen atom, methyl group, ethyl group, or butyl group. Compounds in which either $R'_1$ to $R'_{10}$ are all hydrogen atoms, or one of $R'_1$ to $R'_{10}$ is a methyl group, ethyl group or butyl group, and the remainder of $R'_1$ to $R'_{10}$ are hydrogen atoms are preferred.

In the present invention, the description "dicarboxylic acid represented by the general formula (1) or (2) or a derivative thereof" refers to at least one of a dicarboxylic acid represented by the general formula (1) or a derivative thereof, or a dicarboxylic acid represented by the general formula (2) or a derivative thereof, and may also include both a dicarboxylic acid represented by the general formula (1) or a derivative thereof, and a dicarboxylic acid represented by the general formula (2) or a derivative thereof. According to the present invention, provided the mixture comprises the endo isomer and the exo isomer of a dicarboxylic acid represented by the general formula (1) or (2) or a derivative thereof, the present invention is capable of separating the endo and exo isomers regardless of the mixture.

There are no particular restrictions on the mixture of the general formula (1) or (2) type. A dicarboxylic acid represented by the general formula (1) or a derivative thereof can be obtained by a Diels-Alder reaction, which is described below, between maleic acid or maleic anhydride and cyclopentadiene, and a dicarboxylic acid represented by the general formula (2) or a derivative thereof can be obtained by a hydrogenation reaction, which is described below, of the dicarboxylic acid represented by the general formula (1) or a derivative thereof.

In the present invention, in the general formula (1), compounds in which either $R_1$ to $R_8$ are all hydrogen atoms, or one of $R_1$ to $R_8$ is a methyl group are preferred. Furthermore, in the general formula (2), compounds in which either $R'_1$ to $R'_{10}$ are all hydrogen atoms, or one of $R'_1$ to $R'_{10}$ is a methyl group are preferred.

In the present invention, the endo isomer of the general formula (1) or (2) type and the exo isomer of the general formula (1) or (2) type can each use either a single compound, or a mixture of two or more different compounds.

Although the mixing ratio between the endo isomer of the general formula (1) or (2) type and the exo isomer of the general formula (1) or (2) type is arbitrary, the exo stereoisomeric ratio [%] for the general formula (1) or (2) type, represented by the expression [exo isomer of the general formula (1) or (2) type]/([exo isomer of the general formula (1) or (2) type]+[endo isomer of the general formula (1) or (2) type])×100 [%] is preferably within a range from at least 1% to no more than 99%. Ratios of at least 3% but no more than 97% are even more desirable.

In the present invention, a derivative of a dicarboxylic acid represented by the general formula (1) or (2) refers to an anhydride or a salt of the dicarboxylic acid represented by the general formula (1) or (2). The salt of the dicarboxylic acid may be either a monocarboxylate salt or a dicarboxylate salt of the dicarboxylic acid, or may also be a mixture of monocarboxylate and dicarboxylate salts. Examples of the salt of the dicarboxylic acid include salts of the dicarboxylic acid and an alkali metal such as sodium, potassium or lithium, salts of the dicarboxylic acid and an alkaline earth metal such as magnesium or calcium, salts of the dicarboxylic acid and an ammonium such as an ammonium, trimethylammonium or tetramethylammonium. These salts can be used either alone, or in combinations of two or more different salts.

In the present invention, the dicarboxylic acid represented by the general formula (1) or (2) or a derivative thereof comprises at least one material selected from the group consisting of a dicarboxylic acid represented by the general formula (1) or (2), an anhydride of the dicarboxylic acid, and a salt of the dicarboxylic acid, and may also comprise all of a dicarboxylic acid represented by the general formula (1) or (2), an anhydride of the dicarboxylic acid, and a salt of the dicarboxylic acid.

A mixture of the general formula (1) or (2) type according to the present invention preferably comprises at least one of an endo isomer of a dicarboxylic acid represented by the general formula (1) or (2), an endo isomer of the anhydride of the dicarboxylic acid, an exo isomer of the dicarboxylic acid, and an exo isomer of the anhydride of the dicarboxylic acid.

Furthermore, besides the endo isomer of the general formula (1) or (2) type and the exo isomer of the general formula (1) or (2) type, the mixture of the general formula (1) or (2) type may also include small quantities of other compounds such as the raw materials used in the Diels-Alder reaction, including maleic acid, maleic anhydride, citraconic acid, citraconic anhydride, cyclopentadiene, methylcyclopentadiene, dicyclopentadiene, methylcyclopentadiene dimer, as well as compounds produced by hydrogenating the above compounds, such as succinic acid, succinic anhydride, methylsuccinic acid, methylsuccinic anhydride, tricyclo[5.2.1.0$^{2,6}$]decane, and hydrogenated products of methylcyclopentadiene dimer, provided these quantities are small enough to enable the separation of the endo isomer of the general formula (1) or (2) type and the exo isomer of the general formula (1) or (2) type.

Examples of the basic compound used in the present invention include alkali metal hydroxides such as lithium hydroxide, sodium hydroxide and potassium hydroxide, carbonates such as lithium hydrogencarbonate, sodium hydrogencarbonate, potassium hydrogencarbonate, lithium carbonate, sodium carbonate and potassium carbonate, acetates such as lithium acetate, sodium acetate and potassium acetate, phosphates such as lithium phosphate, sodium phosphate and potassium phosphate, amines such as trimethylamine, triethylamine, pyridine and piperidine, and ammonia. In the present invention, the use of an alkali metal hydroxide is preferred, and the use of sodium hydroxide is particularly desirable. The basic compound is preferably added in liquid form, is even more preferably added as a solution, and is most preferably added as an aqueous solution. In those cases where the basic compound is added as a solution, the solvent used in dissolution of the basic compound is included within the quantity of the solvent described below.

The basic compound is preferably used in a quantity that achieves at least 0.35 equivalents and no more than 8 equivalents relative to the mixture of the general formula (1) or (2) type. If the quantity used of the basic compound is less than the above range, the endo isomer of the general formula (1) or (2) type may not dissolve satisfactorily, making separation difficult, whereas if the quantity exceeds the above range, the stereoisomeric ratio of the obtained solid phase may decrease.

The equivalent weights prescribed in the present invention, relative to either the mixture of the general formula (1) or (2) type, or the endo isomer of the general formula (1) or (2) type, refer to equivalent weights following stirring and mixing of the mixture of the general formula (1) or (2) type with the basic compound and the solvent, meaning that in those cases where the mixture of the general formula (1) or (2) type includes a salt of the dicarboxylic acid from the outset, that salt is included within the equivalent weights of the basic compound prescribed in the present invention.

In the present invention, water is preferably used as the solvent, although the use of a water-miscible solvent in combination with water is also suitable. Examples of suitable water-miscible solvents include alcohols such as methanol, ethanol, propyl alcohol, isopropyl alcohol and butanol, ketones such as acetone, methyl ethyl ketone and methyl isobutyl ketone, glycol derivatives such as ethylene glycol monomethyl ether and ethylene glycol monoethyl ether, esters such as ethyl acetate and isopropyl acetate, amides such as N,N-dimethylformamide and N-methylpyrrolidone, as well as dimethylsulfoxide and acetonitrile.

Although the quantity of the solvent varies depending on the water-miscible solvent added and the quantity thereof, at least 0.7 g and no more than 20 g is preferably used per 6 mmol of the mixture of the general formula (1) or (2) type. If the quantity used of the solvent is less than the above range then the reaction between acid and base may not progress adequately, making separation difficult, whereas if the quantity exceeds the above range, the entire mixture may dissolve, making separation impossible.

Although the mixture of the general formula (1) or (2) type, the basic compound and the solvent may be mixed together in any order, the mixture and the solvent are preferably mixed together first, with the basic compound then added in solution form to the mixed solution with constant stirring.

The temperature during stirring may be at least 0° C., and no more than either 120° C. or the boiling point of the solvent, but is preferably at least 30° C. and no more than 90° C.

Because, if reaction is conducted at a temperature exceeding 120° C., there is a possibility that a stereoisomerization reaction of the dicarboxylic acid represented by the general formula (1) or (2) or a derivative thereof may occur, or that decomposition of the dicarboxylic acid represented by the general formula (1) or (2) or a derivative thereof may occur.

The stirring period is preferably within a range from 5 minutes to 40 hours. If this period is less than 5 minutes then the reaction between the dicarboxylic acid represented by the general formula (1) or (2) or a derivative thereof and the basic compound may not progress adequately, making separation difficult.

By conducting this step, the majority of the endo isomer of the general formula (1) or (2) type dissolves in the solvent, whereas the majority of the exo isomer of the general formula (1) or (2) type does not dissolve, meaning the endo isomer and the exo isomer separate, yielding a suspension. By subjecting the obtained suspension to either filtration or another simple method for separating the liquid and the solid, a salt of the endo isomer of the dicarboxylic acid represented by the general formula (1) or (2), and a salt of the exo isomer of the dicarboxylic acid represented by the general formula (1) or (2) can be obtained.

For example, in the case of a mixture comprising a dicarboxylic acid represented by the general formula (1) or a derivative thereof, and a dicarboxylic acid represented by the general formula (2) or a derivative thereof, separation can be achieved into a liquid phase comprising a mixture of the endo isomer of the general formula (1) type and the endo isomer of the general formula (2) type, and a solid phase comprising a mixture of the exo isomer of the general formula (1) type and the exo isomer of the general formula (2) type.

For example, a mixture comprising 5-norbornene-endo-2,3-dicarboxylic acid or a derivative thereof, and norbornane-exo-2,3-dicarboxylic acid or a derivative thereof can be separated into a liquid phase containing the 5-norbornene-endo-2,3-dicarboxylic acid or a derivative thereof, and a solid phase containing the norbornane-exo-2,3-dicarboxylic acid or a derivative thereof, and similarly, a mixture comprising 5-norbornene-endo-2,3-dicarboxylic acid or a derivative thereof, 5-norbornene-exo-2,3-dicarboxylic acid or a derivative thereof, and norbornane-exo-2,3-dicarboxylic acid or a derivative thereof can be separated into a liquid phase containing the 5-norbornene-endo-2,3-dicarboxylic acid or a derivative thereof, and a solid phase containing the 5-norbornene-exo-2,3-dicarboxylic acid or a derivative thereof and the norbornane-exo-2,3-dicarboxylic acid or a derivative thereof.

The derivative of the dicarboxylic acid represented by the general formula (1) or (2) is separated as a salt, and the separated endo isomer of the salt of the dicarboxylic acid represented by the general formula (1), exo isomer of the salt of the dicarboxylic acid represented by the general formula (1), endo isomer of the salt of the dicarboxylic acid represented by the general formula (2), or exo isomer of the salt of the dicarboxylic acid represented by the general formula (2) can be converted to the corresponding endo isomer of the dicarboxylic acid represented by the general formula (1), exo isomer of the dicarboxylic acid represented by the general formula (1), endo isomer of the dicarboxylic acid represented by the general formula (2), or exo isomer of the dicarboxylic acid represented by the general formula (2) by mixing with an acid such as hydrochloric acid, sulfuric acid, phosphoric acid, or acetic acid. For example, a salt of 5-norbornene-endo-2,3-dicarboxylic acid, a salt of 5-norbornene-exo-2,3-dicarboxylic acid, a salt of norbornane-endo-2,3-dicarboxylic acid, or a salt of norbornane-exo-2,3-dicarboxylic acid can be converted to 5-norbornene-endo-2,3-dicarboxylic acid, 5-norbornene-exo-2,3-dicarboxylic acid, norbornane-endo-2,3-dicarboxylic acid, or norbornane-exo-2,3-dicarboxylic acid respectively, by mixing with an acid such as hydrochloric acid, sulfuric acid, phosphoric acid, or acetic acid.

Specifically, by dissolving the endo isomer or the exo isomer of the salt of the dicarboxylic acid in an aqueous solution containing acid at 40 to 100° C., stirring the solution for a period of 1 minute to 40 hours, and then cooling the solution to 0 to 35° C., the corresponding endo isomer or exo isomer of the dicarboxylic acid can be precipitated as crystals.

In addition, if desired, the obtained endo isomer of the dicarboxylic acid represented by the general formula (1), exo isomer of the dicarboxylic acid represented by the general formula (1), endo isomer of the dicarboxylic acid represented by the general formula (2), or exo isomer of the dicarboxylic acid represented by the general formula (2) can be converted to the corresponding endo isomer of the anhydride of the dicarboxylic acid represented by the general formula (1), exo isomer of the anhydride of the dicarboxylic acid represented by the general formula (1), endo isomer of the anhydride of the dicarboxylic acid represented by the general formula (2), or exo isomer of the anhydride of the dicarboxylic acid represented by the general formula (2) respectively by a typical method such as heating, either alone or in combination with acetic anhydride, conversion to a monoester within a solvent followed by heating, or dehydration under high temperature and high pressure conditions. For example, the obtained 5-norbornene-endo-2,3-dicarboxylic acid, 5-norbornene-exo-2,3-dicarboxylic acid, norbornane-endo-2,3-dicarboxylic acid, or norbornane-exo-2,3-dicarboxylic acid can be converted to 5-norbornene-endo-2,3-dicarboxylic anhydride, 5-norbornene-exo-2,3-dicarboxylic anhydride, norbornane-endo-2,3-dicarboxylic anhydride, or norbornane-exo-2,3-dicarboxylic anhydride respectively, by a typical method such as heating, either alone or in combination with acetic anhydride, or conversion to a monoester within a solvent followed by heating.

Specifically, by dissolving the endo isomer or the exo isomer of the dicarboxylic acid in acetic anhydride at 40 to 100° C., stirring the solution for a period of 1 minute to 40 hours, and then cooling the solution to 0 to 35° C., the corresponding endo isomer or exo isomer of the dicarboxylic anhydride can be precipitated as crystals.

Furthermore, if desired, the separated endo isomer of the salt of the dicarboxylic acid represented by the general formula (1), exo isomer of the salt of the dicarboxylic acid represented by the general formula (1), endo isomer of the salt of the dicarboxylic acid represented by the general formula (2), or exo isomer of the salt of the dicarboxylic acid represented by the general formula (2) may also be converted to the corresponding endo isomer of the anhydride of the dicarboxylic acid represented by the general formula (1), exo isomer of the anhydride of the dicarboxylic acid represented by the general formula (1), endo isomer of the anhydride of the dicarboxylic acid represented by the general formula (2), or exo isomer of the anhydride of the dicarboxylic acid represented by the general formula (2) respectively by a typical method such as heating, either alone or in combination with acetic anhydride.

Examples of preferred embodiments of the separation method of the present invention include those described below.

I. A method of separating the endo isomer and the exo isomer of a dicarboxylic acid represented by the general formula (1) or a derivative thereof, comprising the step of stirring and mixing a mixture (hereafter also referred to as the "mixture of the general formula (1) type"), comprising mainly the endo isomer of the dicarboxylic acid represented by the general formula (1) or a derivative thereof (hereafter also referred to as the "endo isomer of the general formula (1) type") and the exo isomer of the dicarboxylic acid represented by the general formula (1) or a derivative thereof (hereafter also referred to as the "exo isomer of the general formula (1) type"), with a basic compound and a solvent.

II. A method of separating the endo isomer and the exo isomer of a dicarboxylic acid represented by the general formula (2) or a derivative thereof, comprising the step of stirring and mixing a mixture (hereafter also referred to as the "mixture of the general formula (2) type"), comprising mainly the endo isomer of the dicarboxylic acid represented by the general formula (2) or a derivative thereof (hereafter also referred to as the "endo isomer of the general formula (2) type") and the exo isomer of the dicarboxylic acid represented by the general formula (2) or a derivative thereof (hereafter also referred to as the "exo isomer of the general formula (2) type"), with a basic compound and a solvent.

As follows is a description of each of the preferred embodiments of the present invention.

I. Method of separating an endo isomer and an exo isomer, comprising the step of stirring and mixing a mixture of the general formula (1) type, a basic compound, and a solvent.

There are no particular restrictions on the mixture of the general formula (1) type used in the present invention, and any mixture may be used. For example, there are no particular restrictions on a mixture comprising mainly 5-norbornene-endo-2,3-dicarboxylic acid or a derivative thereof and 5-norbornene-exo-2,3-dicarboxylic acid or a derivative thereof, wherein $R_1$ to $R_8$ are all hydrogen atoms, and the mixture obtained by a Diels-Alder reaction between maleic acid or maleic anhydride and cyclopentadiene can be used.

Furthermore, in another example, there are no particular restrictions on a mixture comprising mainly methyl-5-norbornene-endo-2,3-dicarboxylic acid or a derivative thereof and methyl-5-norbornene-exo-2,3-dicarboxylic acid or a derivative thereof, wherein one of $R_1$, or $R_4$ to $R_8$ is a methyl group, and the mixture obtained by a Diels-Alder reaction between maleic acid or maleic anhydride and methylcyclopentadiene can be used.

Furthermore, in yet another example, there are no particular restrictions on a mixture comprising mainly methyl-5-norbornene-endo-2,3-dicarboxylic acid or a derivative thereof and methyl-5-norbornene-exo-2,3-dicarboxylic acid or a derivative thereof, wherein either $R_2$ or $R_3$ is a methyl group, and the mixture obtained by a Diels-Alder reaction between citraconic acid or citraconic anhydride and cyclopentadiene can be used.

These mixtures of the general formula (1) or derivatives thereof may use either the mixtures with a low exo isomer content obtained from the Diels-Alder reaction, or mixtures in which the exo isomer content has been increased by thermal isomerization or photoisomerization of the mixture of the endo isomer and exo isomer obtained from the Diels-Alder reaction. Furthermore, the residue obtained after isolation of one of the structural isomers by recrystallization of the mixture obtained from the Diels-Alder reaction may be used, and the residue obtained after separating one of the structural isomers from the Diels-Alder reaction mixture using the method of the present invention may also be used.

In the present invention, the endo isomer of the general formula (1) type and the exo isomer of the general formula (1) type can each be used either alone, or as a combination of two or more compounds.

Examples of dicarboxylic acids represented by the general formula (1) include 5-norbornene-endo-2,3-dicarboxylic acid, 1-methyl-5-norbornene-endo-2,3-dicarboxylic acid, 2-methyl-5-norbornene-endo-2,3-dicarboxylic acid, 3-methyl-5-norbornene-endo-2,3-dicarboxylic acid, 4-methyl-5-norbornene-endo-2,3-dicarboxylic acid, 5-methyl-5-norbornene-endo-2,3-dicarboxylic acid, 6-methyl-5-norbornene-endo-2,3-dicarboxylic acid, syn-7-methyl-5-norbornene-endo-2,3-dicarboxylic acid, anti-7-methyl-5-norbornene-endo-2,3-dicarboxylic acid, 5-norbornene-2,3-dicarboxylic acid, 1-methyl-5-norbornene-exo-2,3-dicarboxylic acid, 2-methyl-5-norbornene-exo-2,3-dicarboxylic acid, 3-methyl-5-norbornene-exo-2,3-dicarboxylic acid, 4-methyl-5-norbornene-exo-2,3-dicarboxylic acid, 5-methyl-5-norbornene-exo-2,3-dicarboxylic acid, 6-methyl-5-norbornene-exo-2,3-dicarboxylic acid, syn-7-methyl-5-norbornene-exo-2,3-dicarboxylic acid, and anti-7-methyl-5-norbornene-exo-2,3-dicarboxylic acid, as well as compounds containing an ethyl group or butyl group instead of the methyl group in the above compounds.

In the present invention, the use of a mixture comprising 5-norbornene-endo-2,3-dicarboxylic acid or a derivative thereof and 5-norbornene-exo-2,3-dicarboxylic acid or a derivative thereof as the mixture of the general formula (1) type is preferred.

Although the mixing ratio between the endo isomer of the general formula (1) type and the exo isomer of the general formula (1) type is arbitrary, the exo stereoisomeric ratio [%] for the general formula (1) type, represented by the expression [exo isomer of the general formula (1) type]/([exo isomer of the general formula (1) type]+[endo isomer of the general formula (1) type])×100[%] is preferably within a range from at least 1% to no more than 99%. Ratios of at least 3% but no more than 97% are even more desirable.

The basic compound is preferably used in a quantity that achieves at least 0.2 equivalents relative to the endo isomer of the general formula (1) type, and no more than 8 equivalents relative to the mixture of the general formula (1) type. If the quantity used of the basic compound is less than the above range, the endo isomer of the general formula (1) type may not dissolve satisfactorily, making separation difficult, whereas if the quantity exceeds the above range, the stereoisomeric ratio of the obtained solid phase may decrease.

The equivalent weights prescribed in the present invention, relative to either the mixture of the general formula (1) type or the endo isomer of the general formula (1) type, refer to equivalent weights following stirring and mixing of the mixture of the general formula (1) type with the basic compound and the solvent, meaning that in those cases where the mixture of the general formula (1) type includes a salt of the dicarboxylic acid represented by the general formula (1) from the outset, that salt is also included within the equivalent weight of the basic compound prescribed in the present invention. For example, in the case where a mixture of 0.9 mols of 5-norbornene-2,3-dicarboxylic acid and 0.1 mols of the monosodium salt of 5-norbornene-2,3-dicarboxylic acid is used as the mixture, in order to achieve a quantity of basic compound of 0.2 equivalents of the mixture, 0.3 mols of sodium hydroxide is added.

Although the quantity of the solvent varies depending on the water-miscible solvent added and the quantity thereof, a preferred quantity is at least 0.7 g relative to 6 mmol of the mixture of the general formula (1) type, and no more than the larger of either 10 g relative to 6 mmol of the mixture of the general formula (1) type, or 20 g relative to 6 mmol of the endo isomer of the general formula (1) type. If the quantity used of the solvent is less than the above range then the reaction between acid and base may not progress adequately, making separation difficult, whereas if the quantity exceeds the above range, the entire mixture may dissolve, making separation impossible.

As follows is a description of particularly preferred usage quantities for the basic compound and the solvent within the method of separating an endo isomer of the general formula (1) type and an exo isomer of the general formula (1) type according to the present invention.

1) In order to obtain the endo isomer of the general formula (1) type, the basic compound is preferably used in a quantity that achieves at least 0.6 equivalents and no more than 8 equivalents relative to the mixture of the general formula (1) type. Furthermore, the solvent is preferably used in a quantity of at least 0.7 g and no more than 10 g relative to 6 mmol of the mixture of the general formula (1) type.

2) In order to obtain the endo isomer of the general formula (1) type with a high degree of purity, the basic compound is preferably used in a quantity that achieves at least 0.6 equivalents and no more than 2 equivalents relative to the mixture of the general formula (1) type. Furthermore, the solvent is preferably used in a quantity of at least 0.7 g relative to 6 mmol of the mixture of the general formula (1) type, and no more than the larger of either 4 g relative to 6 mmol of the mixture of the general formula (1) type, or 8 g relative to 6 mmol of the endo isomer of the general formula (1) type.

3) In order to obtain the exo isomer of the general formula (1) type, the basic compound is preferably used in a quantity that achieves at least 0.2 equivalents relative to the endo isomer of the general formula (1) type, and no more than 8 equivalents relative to the mixture of the general formula (1) type. Furthermore, the solvent is preferably used in a quantity of at least 0.7 g relative to 6 mmol of the mixture of the general formula (1) type, and no more than the larger of either 10 g relative to 6 mmol of the mixture of the general formula (1) type, or 20 g relative to 6 mmol of the endo isomer of the general formula (1) type.

4) In order to obtain the exo isomer of the general formula (1) type, the basic compound is even more preferably used in a quantity that achieves at least 0.85 equivalents relative to the endo isomer of the general formula (1) type, and no more than 2 equivalents relative to the mixture of the general formula (1) type. Furthermore, the solvent is even more preferably used in a quantity of no less than the smaller of 4 g relative to 6 mmol of the mixture of the general formula (1) type, and 8 g relative to 6 mmol of the endo isomer of the general formula (1) type, and no more than 10 g relative to 6 mmol of the mixture of the general formula (1) type.

5) In order to obtain the exo isomer of the general formula (1) type in those cases where the mixture of the general formula (1) type includes the exo isomer of the general formula (1) type at a stereoisomeric ratio of at least 45%, the basic compound is even more preferably used in a quantity that achieves at least 0.2 equivalents relative to the endo isomer of the general formula (1) type, and no more than 0.7 equivalents relative to the mixture of the general formula (1) type. Furthermore, the solvent is even more preferably used in a quantity of at least 8 g and no more than 20 g relative to 6 mmol of the endo isomer of the general formula (1) type.

By conducting this step, the majority of the endo isomer of the general formula (1) type dissolves in the solvent, whereas the majority of the exo isomer of the general formula (1) type does not dissolve, thereby yielding a suspension. By subjecting the obtained suspension to either filtration or another simple method for separating the liquid and the solid, a salt of the endo isomer of the dicarboxylic acid represented by the general formula (1), and a salt of the exo isomer of the dicarboxylic acid represented by the general formula (1) can be separated.

According to the present invention, an endo isomer or isomers of the general formula (1) type and an exo isomer or isomers of the general formula (1) type can be separated from a mixture comprising either one, or two or more endo isomers of the general formula (1) type, and either one, or two or more exo isomers of the general formula (1) type. In the case of the endo isomers, even if a plurality of different compounds represented by the general formula (1) are contained within the mixture, these endo isomers are separated as a mixture (the solid phase) of endo isomers, and similarly, in the case of the exo isomers, even if a plurality of different compounds represented by the general formula (1) are contained within the mixture, these exo isomers are separated as a mixture (the liquid phase) of exo isomers. For example, if the mixture comprises 2-methyl-5-norbornene-endo-2,3-dicarboxylic acid, 2-methyl-5-norbornene-exo-2,3-dicarboxylic acid, and 5-norbornene-exo-2,3-dicarboxylic acid, then the present invention enables separation into the 2-methyl-5-norbornene-endo-2,3-dicarboxylic acid, and a mixture of the 2-methyl-5-norbornene-exo-2,3-dicarboxylic acid and the 5-norbornene-exo-2,3-dicarboxylic acid.

II. Method of separating an endo isomer and an exo isomer, comprising the step of stirring and mixing a mixture of the general formula (2) type, a basic compound, and a solvent.

There are no particular restrictions on the mixture of the general formula (2) type used in the present invention, and any mixture may be used. In the present invention, a mixture obtained by hydrogenation of a mixture of the general formula (1) type can be used as the mixture of the general formula (2) type.

For example, there are no particular restrictions on a mixture comprising norbornane-endo-2,3-dicarboxylic acid or a derivative thereof and norbornane-exo-2,3-dicarboxylic acid or a derivative thereof, wherein $R'_1$ to $R'_{10}$ are all hydrogen atoms, and the mixture obtained by hydrogenating the double bond at position 5 of the aforementioned mixture comprising 5-norbornene-endo-2,3-dicarboxylic acid or a derivative thereof and 5-norbornene-exo-2,3-dicarboxylic acid or a derivative thereof can be used.

Furthermore, in another example, there are no particular restrictions on a mixture comprising methyl-norbornaneendo-2,3-dicarboxylic acid or a derivative thereof and methyl-norbornane-exo-2,3-dicarboxylic acid or a derivative thereof, wherein one of $R'_1$ through $R'_{10}$ is a methyl group, and the mixture obtained by hydrogenating the double bond at position 5 of a mixture comprising methyl-5-norbornene-endo-2,3-dicarboxylic acid or a derivative thereof and methyl-5-norbornene-endo-2,3-dicarboxylic acid or a derivative thereof can be used.

These mixtures of the general formula (2) type may use either mixtures with a low exo isomer content, obtained by hydrogenation of a mixture of the general formula (1) type obtained from a Diels-Alder reaction, or mixtures with an enhanced exo isomer content, obtained by hydrogenation of a mixture of the general formula (1) type obtained from a Diels-Alder reaction followed by thermal isomerization or photoisomerization. Furthermore, the residue obtained after isolation of one of the structural isomers by recrystallization from a mixture of the general formula (2) type may be used, and the residue obtained after separating one of the structural isomers from a mixture of the general formula (2) type using the method of the present invention may also be used.

Hydrogenation uses a hydrogenation catalyst such as a metal catalyst, a metal oxide or sulfide catalyst, or a metal complex catalyst, and is conducted by heating under an atmosphere of hydrogen. The heating temperature is preferably within a range from 40 to 90° C.

In the present invention, the endo isomer of the general formula (2) type and the exo isomer of the general formula (2) type can each be used either alone, or as a combination of two or more compounds.

Examples of dicarboxylic acids represented by the general formula (2) include norbornane-endo-2,3-dicarboxylic acid, 1-methyl-norbornane-endo-2,3-dicarboxylic acid, 2-methyl-norbornane-endo-2,3-dicarboxylic acid, 3-methyl-norbornane-endo-2,3-dicarboxylic acid, 4-methyl-norbornane-endo-2,3-dicarboxylic acid, 5-methyl-norbornane-endo-2,3-dicarboxylic acid, 6-methyl-norbornane-endo-2,3-dicarboxylic acid, syn-7-methyl-norbornane-endo-2,3-dicarboxylic acid, anti-7-methyl-norbornane-endo-2,3-dicarboxylic acid, norbornane-exo-2,3-dicarboxylic acid, 1-methyl-norbornane-exo-2,3-dicarboxylic acid, 2-methyl-norbornane-exo-2,3-dicarboxylic acid, 3-methyl-norbornane-exo-2,3-dicarboxylic acid, 4-methyl-norbornane-exo-2,3-dicarboxylic acid, 5-methyl-norbornane-exo-2,3-dicarboxylic acid, 6-methyl-norbornane-exo-2,3-dicarboxylic acid, syn-7-methyl-norbornane-exo-2,3-dicarboxylic acid, and anti-7-methyl-norbornane-exo-2,3-dicarboxylic acid, as well as compounds containing an ethyl group or butyl group instead of the methyl group in the above compounds.

In the present invention, the use of a mixture comprising norbornane-endo-2,3-dicarboxylic acid or a derivative thereof and norbornane-exo-2,3-dicarboxylic acid or a derivative thereof as the mixture of the general formula (2) type is preferred.

Although the mixing ratio between the endo isomer of the general formula (2) type and the exo isomer of the general formula (2) type is arbitrary, the exo stereoisomeric ratio [%] for the general formula (2) type, represented by the expression [exo isomer of the general formula (2) type]/([exo isomer of the general formula (2) type]+[endo isomer of the general formula (2) type])×100[%] is preferably within a range from at least 1% to no more than 99%. Ratios of at least 10% but no more than 90% are even more desirable.

The basic compound is preferably used in a quantity that achieves at least 0.35 equivalents, and no more than 8 equivalents, relative to the mixture of the general formula (2) type. If the quantity used of the basic compound is less than the above range, the reaction between acid and base may not progress adequately, making separation difficult, whereas if the quantity exceeds the above range, the stereoisomeric ratio of the obtained solid phase may decrease.

The equivalent weights prescribed in the present invention, relative to either the mixture of the general formula (2) type or the endo isomer of the general formula (2) type, refer to equivalent weights following stirring and mixing of the mixture of the general formula (2) type with the basic compound and the solvent, meaning that in those cases where the mixture of the general formula (2) type includes a salt of either the endo isomer or the exo isomer of the dicarboxylic acid represented by the general formula (2) from the outset, that salt is also included within the equivalent weight of the basic compound prescribed in the present invention. For example, in the case where a mixture of 0.9 mols of norbornane-2,3-dicarboxylic acid and 0.1 mols of the monosodium salt of norbornane-2,3-dicarboxylic acid is used as the mixture, in order to achieve a quantity of basic compound of 0.5 equivalents of the mixture, 0.9 mols of sodium hydroxide is added.

Although the quantity of the solvent varies depending on the water-miscible solvent added and the quantity thereof, a preferred quantity is at least 0.7 g and no more than 20 g relative to 6 mmol of the mixture of dicarboxylic acids represented by the general formula (2) or derivatives thereof. If the quantity used of the solvent is less than the above range then the reaction between acid and base may not progress adequately, making separation difficult, whereas if the quantity exceeds the above range, the entire mixture may dissolve, making separation impossible.

By conducting this step, the majority of the endo isomer of the general formula (2) type dissolves in the solvent, whereas the majority of the exo isomer of the general formula (2) type does not dissolve, thereby yielding a suspension. By subjecting the obtained suspension to either filtration or another simple method for separating the liquid and the solid, a salt of the endo isomer of the dicarboxylic acid represented by the general formula (2), and a salt of the exo isomer of the dicarboxylic acid represented by the general formula (2) can be separated.

According to the present invention, an endo isomer or isomers of the general formula (2) type and an exo isomer or isomers of the general formula (2) type can be separated from a mixture comprising either one, or two or more endo isomers of the general formula (2) type, and either one, or two or more exo isomers of the general formula (2) type. In the case of the endo isomers, even if a plurality of different compounds represented by the general formula (2) are contained within the mixture, these endo isomers are separated as a mixture (the solid phase) of endo isomers, and similarly, in the case of the exo isomers, even if a plurality of different compounds represented by the general formula (2) are contained within the mixture, these exo isomers are separated as a mixture (the liquid phase) of exo isomers. For example, if the mixture comprises 2-methyl-norbornane-endo-2,3-dicarboxylic acid, 2-methyl-norbornane-exo-2,3-dicarboxylic acid, and norbornane-exo-2,3-dicarboxylic acid, then the present invention enables separation into the 2-methyl-norbornane-endo-2,3-dicarboxylic acid, and a mixture of the 2-methyl-norbornane-exo-2,3-dicarboxylic acid and the norbornane-exo-2,3-dicarboxylic acid.

Next is a description of another aspect of the present invention. This method of the present invention for separating the endo isomer and the exo isomer of a salt of a dicarboxylic acid represented by the general formula (1) or (2) comprises the step of stirring and mixing a mixture (hereafter also referred to as a "mixture of the general formula (1) or (2) salt") comprising mainly the endo isomer of the salt of the dicarboxylic acid represented by the general formula (1) or (2) (hereafter also referred to as the "endo isomer the general formula (1) or (2) salt"), and the exo isomer of the salt of the dicarboxylic acid represented by the general formula (1) or (2) (hereafter also referred to as the "exo isomer of general formula (1) or (2) salt"), with a solvent. Thus, the endo isomer and the exo isomer of the salt of dicarboxylic acid represented by the general formula (1) may be stirred and mixed with a solvent.

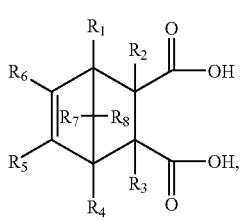

(1)

In the general formula (1), $R_1$ to $R_8$ represent a hydrogen atom, methyl group, ethyl group, or butyl group. Compounds in which either $R_1$ to $R_8$ are all hydrogen atoms, or one of $R_1$ to $R_8$ is a methyl group, ethyl group or butyl group, and the remainder of $R_1$ to $R_8$ are hydrogen atoms are preferred. Likewise, the endo isomer and the exo isomer of the salt of dicarboxylic acid represented by the general formula (2) may be stirred and mixed with a solvent.

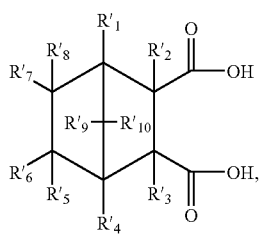

(2)

In the general formula (2), $R'_1$ to $R'_{10}$ represent a hydrogen atom, methyl group, ethyl group, or butyl group. Compounds in which either $R'_1$ to $R'_{10}$ are all hydrogen atoms, or one of $R'_1$ to $R'_{10}$ is a methyl group, ethyl group or butyl group, and the remainder of $R'_1$ to $R'_{10}$ are hydrogen atoms are preferred.

In the present invention, the description "salt of a dicarboxylic acid represented by the general formula (1) or (2)" refers to at least one of a salt of a dicarboxylic acid represented by the general formula (1), or a salt of a dicarboxylic acid represented by the general formula (2), and may also include both a salt of a dicarboxylic acid represented by the general formula (1) and a salt of a dicarboxylic acid represented by the general formula (2). According to the present invention, provided the mixture comprises mainly the endo isomer and the exo isomer of a salt of a dicarboxylic acid represented by the general formula (1) or (2), the present invention is capable of separating the endo and exo isomers regardless of the mixture.

In the present invention, a salt of a dicarboxylic acid represented by the general formula (1) or (2) may be either a monocarboxylate salt or a dicarboxylate salt of the dicarboxylic acid, or may also be a mixture of monocarboxylate and dicarboxylate salts.

In this method, because a mixture is used in which the endo isomer and the exo isomer of the dicarboxylic acid represented by the general formula (1) or (2) exist as salts, separation can be achieved by stirring and mixing the mixture with a solvent, although if required, a basic compound may also be added.

The same salts of dicarboxylic acids represented by the general formula (1) or (2), together with the same solvents, basic compounds and water-miscible solvents as those used in the aforementioned method of separating an endo isomer of the general formula (1) or (2) type and an exo isomer of the general formula (1) or (2) type can be used, and other factors such as the mixing method and stirring period may also be the same.

Although the quantity of the solvent varies depending on the water-miscible solvent added and the quantity thereof, a preferred quantity is at least 0.7 g relative to 6 mmol of the mixture of the general formula (1) or (2) salt, and no more than the larger of either 10 g relative to 6 mmol of the mixture of the general formula (1) or (2) salt, or 20 g relative to 6 mmol of the endo isomer the general formula (1) or (2) salt.

In the same manner as the aforementioned method of separating an endo isomer of the general formula (1) or (2) type and an exo isomer of the general formula (1) or (2) type, this aspect of the present invention utilizes the difference in solubility in the solvent for the salts of the dicarboxylic acid, and by using the separation method of this aspect of the present invention, the endo isomer the general formula (1) or (2) salt can be obtained as the liquid phase, and the exo isomer of general formula (1) or (2) salt can be obtained as the solid phase.

By conducting this step, the majority of the endo isomer the general formula (1) or (2) salt dissolves in the solvent, whereas the majority of the exo isomer of general formula (1) or (2) salt does not dissolve, meaning the endo isomer and the exo isomer separate, yielding a suspension. By subjecting the obtained suspension to either filtration or another simple method for separating the liquid and the solid, the salt of the endo isomer of the dicarboxylic acid represented by the general formula (1) or (2), and the salt of the exo isomer of the dicarboxylic acid represented by the general formula (1) or (2) can be separated.

For example, in the case of a mixture comprising a salt of a dicarboxylic acid represented by the general formula (1) and a salt of a dicarboxylic acid represented by the general formula (2), separation can be achieved into a liquid phase comprising a mixture of the endo isomer of the general formula (1) type and the endo isomer of the general formula (2) type, and a solid phase comprising a mixture of the exo isomer of the general formula (1) type and the exo isomer of the general formula (2) type.

For example, a mixture comprising a salt of 5-norbornene-endo-2,3-dicarboxylic acid and a salt of norbornane-exo-2,3-dicarboxylic acid can be separated into a liquid phase containing the salt of 5-norbornene-endo-2,3-dicarboxylic acid, and a solid phase containing the salt of norbornane-exo-2,3-dicarboxylic acid, and similarly, a mixture comprising a salt of 5-norbornene-endo-2,3-dicarboxylic acid, a salt of 5-norbornene-exo-2,3-dicarboxylic acid, and a salt of norbornane-exo-2,3-dicarboxylic acid can be separated into a liquid phase containing the salt of 5-norbornene-endo-2,3-dicarboxylic acid, and a solid phase containing the salt of 5-norbornene-exo-2,3-dicarboxylic acid and the salt of norbornane-exo-2, 3-dicarboxylic acid.

If desired, the obtained salt of the dicarboxylic acid represented by the general formula (1) or salt of the dicarboxylic acid represented by the general formula (2) may be converted to either the corresponding dicarboxylic acid or dicarboxylic anhydride, using the methods described above.

Examples of preferred embodiments of the separation method of this aspect of the present invention include those described below.

i. A method of separating the endo isomer and the exo isomer of a salt of a dicarboxylic acid represented by the general formula (1), comprising the step of stirring and mixing a mixture (hereafter also referred to as the "mixture of the general formula (1) salt") comprising mainly the endo isomer of the salt of the dicarboxylic acid represented by the general formula (1) (hereafter also referred to as the "endo isomer of the general formula (1) salt"), and the exo isomer of the salt of the dicarboxylic acid represented by the general formula (1) (hereafter also referred to as the "exo isomer of the general formula (1) salt") with a solvent.

According to this invention, for example, the salt of 5-norbornene-endo-2,3-dicarboxylic acid can be obtained as the liquid phase, and the salt of 5-norbornene-exo-2,3-dicarboxylic acid can be obtained as the solid phase.

ii. A method of separating the endo isomer and the exo isomer of a salt of a dicarboxylic acid represented by the general formula (2), comprising the step of stirring and mixing a mixture (hereafter also referred to as the "mixture of the general formula (2) salt") comprising mainly the endo isomer of the salt of the dicarboxylic acid represented by the general formula (2) (hereafter also referred to as the "endo isomer of the general formula (2) salt"), and the exo isomer of the salt of the dicarboxylic acid represented by the general formula (2) (hereafter also referred to as the "exo isomer of the general formula (2) salt") with a solvent.

According to this invention, for example, the salt of norbornane-endo-2,3-dicarboxylic acid can be obtained as the liquid phase, and the salt of norbornane-exo-2,3-dicarboxylic acid can be obtained as the solid phase.

According to the separation method of the present invention, either stereoisomer can be obtained easily, efficiently, and with a high degree of purity from a mixture comprising mainly the endo isomer of a dicarboxylic acid represented by the general formula (1) or (2) or a derivative thereof and the exo isomer of a dicarboxylic acid represented by the general formula (1) or (2) or a derivative thereof. Furthermore, according to the separation method of the present invention, either stereoisomer can be obtained easily, efficiently, and with a high degree of purity from a mixture comprising mainly the endo isomer of a salt of a dicarboxylic acid represented by the general formula (1) or (2) and the exo isomer of a salt of a dicarboxylic acid represented by the general formula (1) or (2). In particular, the exo isomer of a dicarboxylic acid represented by the general formula (1) or (2) or a derivative thereof, which has proven difficult to obtain using conventional methods, can be obtained easily, efficiently, and with a high degree of purity.

In particular, by prescribing the quantities used of the basic compound and the solvent, either one of the stereoisomers can be obtained even more easily and efficiently, and with an even higher degree of purity.

According to the present invention, either one of the stereoisomers can be obtained as a mixture in which the stereoisomeric ratio for that isomer has been increased. In those cases where an endo isomer of a dicarboxylic acid represented by the general formula (1) or (2) or a derivative thereof is targeted, the endo stereoisomeric ratio within the product mixture is preferably at least 90%, whereas in those cases where an exo isomer of a dicarboxylic acid represented by the general formula (1) or (2) or a derivative thereof is targeted, the exo stereoisomeric ratio within the product mixture is preferably at least 80%.

EXAMPLES

As follows is a description of the present invention based on a series of examples, although the present invention is in no way limited by these examples.

Furthermore, in order to determine the ratio between the endo isomer of a dicarboxylic acid represented by the general formula (1) or (2) or a derivative thereof, and the exo isomer of a dicarboxylic acid represented by the general formula (1) or (2) or a derivative thereof, the mixture was subjected to measurement using high performance liquid chromatography.

The column used was a Wakosil-II 5C18AR column manufactured by Wako Pure Chemical Industries Ltd., the eluent was a solution comprising a distilled water/acetonitrile mixture with a volumetric ratio of 8/2 to which had been added 0.05 mol/L of trifluoroacetic acid, and the detector unit was an ultraviolet-visible spectroscopic detector 875-UV manufactured by Jasco Corporation.

Furthermore, the endo stereoisomeric ratio [%] for the general formula (1) type=[endo isomer of the dicarboxylic acid represented by the general formula (1) or a derivative thereof]/([exo isomer of the dicarboxylic acid represented by the general formula (1) or a derivative thereof]+[endo isomer of the dicarboxylic acid represented by the general formula (1) or a derivative thereof])×100[%], and the exo stereoisomeric ratio [%] for the general formula (1) type=[exo isomer of the dicarboxylic acid represented by the general formula (1) or a derivative thereof]/([exo isomer of the dicarboxylic acid represented by the general formula (1) or a derivative thereof]+[endo isomer of the dicarboxylic acid represented by the general formula (1) or a derivative thereof])×100[%].

Similarly, the endo stereoisomeric ratio [%] for the general formula (2) type=[endo isomer of the dicarboxylic acid represented by the general formula (2) or a derivative thereof]/([exo isomer of the dicarboxylic acid represented by the general formula (2) or a derivative thereof]+[endo isomer of the dicarboxylic acid represented by the general formula (2) or a derivative thereof])×100[%], and the exo stereoisomeric ratio [%] for the general formula (2) type=[exo isomer of the dicarboxylic acid represented by the general formula (2) or a derivative thereof]/([exo isomer of the dicarboxylic acid represented by the general formula (2) or a derivative thereof]+[endo isomer of the dicarboxylic acid represented by the general formula (2) or a derivative thereof])×100[%].

[Examples Using 5-Norbornene-2,3-Dicarboxylic Anhydride as the Mixture]

5-norbornene-2,3-dicarboxylic anhydride was used as the dicarboxylic acid represented by the general formula (1) or a derivative thereof.

Example 1

To 10.0 g of 5-norbornene-2,3-dicarboxylic anhydride (exo stereoisomeric ratio for the general formula (1) type=26%) were added 33.6 g of water and 16.3 g of a 30 wt % aqueous solution of sodium hydroxide (1.0 equivalents relative to the 5-norbornene-2,3-dicarboxylic anhydride mixture, 1.4 equivalents relative to 5-norbornene-endo-2,3-dicarboxylic anhydride), and the mixture was stirred at 70° C. for 10 minutes. The solid was then separated by filtration and dried. The obtained solid was 1.17 g (exo stereoisomeric ratio for the general formula (1) type=88%).

Example 2

To 10.0 g of 5-norbornene-2,3-dicarboxylic anhydride (exo stereoisomeric ratio for the general formula (1) type=75%) were added 11.1 g of water and 16.3 g of a 30 wt % aqueous solution of sodium hydroxide (1.0 equivalents relative to the 5-norbornene-2,3-dicarboxylic anhydride mixture, 4.0 equivalents relative to 5-norbornene-endo-2,3-dicarboxylic anhydride), and the mixture was stirred at 70° C. for 10 minutes. The solid was then separated by filtration and dried. The obtained solid was 10.33 g (exo stereoisomeric ratio for the general formula (1) type=84%).

Example 3

With the exception of using 33.7 g of water, preparation was conducted in the same manner as the example 2. The obtained solid was 7.21 g (exo stereoisomeric ratio for the general formula (1) type=92%).

Example 4

To 10.0 g of 5-norbornene-2,3-dicarboxylic anhydride (exo stereoisomeric ratio for the general formula (1) type=48%) were added 33.6 g of water and 16.3 g of a 30 wt % aqueous solution of sodium hydroxide (1.0 equivalents relative to the 5-norbornene-2,3-dicarboxylic anhydride mixture, 1.9 equivalents relative to 5-norbornene-endo-2,3-dicarboxylic anhydride), and the mixture was stirred at 70° C. for 10 minutes. The solid was then separated by filtration and dried. The obtained solid was 4.48 g (exo stereoisomeric ratio for the general formula (1) type=88%).

Example 5

To 10.0 g of 5-norbornene-2,3-dicarboxylic anhydride (exo stereoisomeric ratio for the general formula (1) type=75%) were added 39.3 g of water and 8.2 g of a 30 wt % aqueous solution of sodium hydroxide (0.5 equivalents relative to the 5-norbornene-2,3-dicarboxylic anhydride mixture, 2.0 equivalents relative to 5-norbornene-endo-2,3-dicarboxylic anhydride), and the mixture was stirred at 70° C. for 10 minutes. The solid was then separated by filtration and dried. The obtained solid was 6.62 g (exo stereoisomeric ratio for the general formula (1) type=86%).

Example 6

To 10.0 g of 5-norbornene-2,3-dicarboxylic anhydride (exo stereoisomeric ratio for the general formula (1) type=75%) were added 27.9 g of water and 24.5 g of a 30 wt % aqueous solution of sodium hydroxide (1.5 equivalents relative to the 5-norbornene-2,3-dicarboxylic anhydride mixture, 6.0 equivalents relative to 5-norbornene-endo-2,3-dicarboxylic anhydride), and the mixture was stirred at 70° C. for 10 minutes. The solid was then separated by filtration and dried. The obtained solid was 9.90 g (exo stereoisomeric ratio for the general formula (1) type=91%).

Example 7

To 10.0 g of 5-norbornene-2,3-dicarboxylic anhydride (exo stereoisomeric ratio for the general formula (1) type=75%) were added 16.8 g of water and 8.2 g of a 30 wt % aqueous solution of sodium hydroxide (0.5 equivalents relative to the 5-norbornene-2,3-dicarboxylic anhydride mixture, 2.0 equivalents relative to 5-norbornene-endo-2,3-dicarboxylic anhydride), and the mixture was stirred at 70° C. for 10 minutes. The solid was then separated by filtration and dried. The obtained solid was 9.42 g (exo stereoisomeric ratio for the general formula (1) type=79%).

Example 8

To 10.0 g of 5-norbornene-2,3-dicarboxylic anhydride (exo stereoisomeric ratio for the general formula (1) type=48%) were added 42.4 g of water and 4.1 g of a 30 wt % aqueous solution of sodium hydroxide (0.25 equivalents relative to the 5-norbornene-2,3-dicarboxylic anhydride mixture, 0.5 equivalents relative to 5-norbornene-endo-2,3-dicarboxylic anhydride), and the mixture was stirred at 70° C. for 10 minutes. The solid was then separated by filtration and dried. The obtained solid was 2.81 g (exo stereoisomeric ratio for the general formula (1) type=89%).

Example 9

To 10.0 g of 5-norbornene-2,3-dicarboxylic anhydride (exo stereoisomeric ratio for the general formula (1) type=75%) were added 21.0 g of water and 2.1 g of a 30 wt % aqueous solution of sodium hydroxide (0.13 equivalents relative to the 5-norbornene-2,3-dicarboxylic anhydride mixture, 0.5 equivalents relative to 5-norbornene-endo-2,3-dicarboxylic anhydride), and the mixture was stirred at 70° C. for 10 minutes. The solid was then separated by filtration and dried. The obtained solid was 5.82 g (exo stereoisomeric ratio for the general formula (1) type=96%).

Example 10

To 10.0 g of 5-norbornene-2,3-dicarboxylic anhydride (endo stereoisomeric ratio for the general formula (1) type=78%) were added 13.6 g of water and 16.4 g of a 30 wt % aqueous solution of sodium hydroxide (1.0 equivalents relative to the 5-norbornene-2,3-dicarboxylic anhydride mixture, 1.3 equivalents relative to 5-norbornene-endo-2,3-dicarboxylic anhydride), and the mixture was stirred at 70° C. for 10 minutes. The solid was then separated by filtration. The endo stereoisomeric ratio for the 5-norbornene-2,3-dicarboxylic acid contained within the resulting filtrate was 95%. Furthermore, the filtration residue was 4.21 g (exo stereoisomeric ratio for the general formula (1) type 46%).

Example 11

To 10.0 g of 5-norbornene-2,3-dicarboxylic anhydride (endo stereoisomeric ratio for the general formula (1) type=25%) were added 13.6 g of water and 16.3 g of a 30 wt % aqueous solution of sodium hydroxide (1.0 equivalents relative to the 5-norbornene-2,3-dicarboxylic anhydride mixture, 4.0 equivalents relative to 5-norbornene-endo-2,3-dicarboxylic anhydride), and the mixture was stirred at 70° C. for 10 minutes. The solid was then separated by filtration. The endo stereoisomeric ratio for the 5-norbornene-2,3-dicarboxylic acid contained within the resulting filtrate was 87%. Furthermore, the filtration residue was 11.15 g (exo stereoisomeric ratio for the general formula (1) type=89%).

Example 12

To 10.0 g of 5-norbornene-2,3-dicarboxylic anhydride (endo stereoisomeric ratio for the general formula (1)

type=78%) were added 1.1 g of water and 16.3 g of a 30 wt % aqueous solution of sodium hydroxide (1.0 equivalents relative to the 5-norbornene-2,3-dicarboxylic anhydride mixture, 1.3 equivalents relative to 5-norbornene-endo-2,3-dicarboxylic anhydride), and the mixture was stirred at 70° C. for 10 minutes. The solid was then separated by filtration. The endo stereoisomeric ratio for the 5-norbornene-2,3-dicarboxylic acid contained within the resulting filtrate was 96%. Furthermore, the filtration residue was 12.11 g (exo stereoisomeric ratio for the general formula (1) type=26%).

Example 13

To 10.0 g of 5-norbornene-2,3-dicarboxylic anhydride (endo stereoisomeric ratio for the general formula (1) type=25%) were added 1.1 g of water and 16.3 g of a 30 wt % aqueous solution of sodium hydroxide (1.0 equivalents relative to the 5-norbornene-2,3-dicarboxylic anhydride mixture, 4.0 equivalents relative to 5-norbornene-endo-2,3-dicarboxylic anhydride), and the mixture was stirred at 70° C. for 10 minutes. The solid was then separated by filtration. The endo stereoisomeric ratio for the 5-norbornene-2,3-dicarboxylic acid contained within the resulting filtrate was 83%. Furthermore, the filtration residue was 12.43 g (exo stereoisomeric ratio for the general formula (1) type=81%).

Example 14

To 20.0 g of 5-norbornene-1,4-dicarboxylic anhydride (exo stereoisomeric ratio for the general formula (1) type=48%) were added 27.2 g of distilled water and 32.6 g of a 30 wt % aqueous solution of sodium hydroxide (1.0 equivalents relative to the 5-norbornene-2,3-dicarboxylic anhydride mixture, 1.9 equivalents relative to 5-norbornene-endo-2,3-dicarboxylic anhydride), and the mixture was stirred at 70° C. for 10 minutes. The solid phase and the liquid phase were then separated by filtration. For the liquid phase, the endo stereoisomeric ratio for the general formula (1) type=95%. The solid phase was dried, and the resulting solid was 13.8 g (exo stereoisomeric ratio for the general formula (1) type=80%). To 10.8 g of this dried solid was added 38.3 g of distilled water, and the mixture was stirred at 70° C. for 10 minutes. The solid phase and the liquid phase were then again separated by filtration. Drying of the solid phase yielded a solid of 6.7 g (exo stereoisomeric ratio for the general formula (1) type=91%).

Example 15

To 29.1 g of disodium 5-norbornene-1,4-dicarboxylate (exo stereoisomeric ratio for the general formula (1) type=46%) was added 57.7 g of distilled water, and the mixture was stirred at 70° C. for 15 minutes. The solid phase and the liquid phase were then separated by filtration. For the liquid phase, the endo stereoisomeric ratio for the general formula (1) type=80%. The solid phase was dried, and the resulting solid was 19.8 g (exo stereoisomeric ratio for the general formula (1) type=67%). To 18.7 g of this dried solid was added 66.3 g of distilled water, and the mixture was stirred at 70° C. for 15 minutes. The solid phase and the liquid phase were then again separated by filtration. Drying of the solid phase yielded a solid of 2.3 g (exo stereoisomeric ratio for the general formula (1) type=90%).

[Examples Using Norbornane-2,3-Dicarboxylic Anhydride as the Mixture]

Norbornane-2,3-dicarboxylic anhydride was used as the dicarboxylic acid represented by the general formula (2) or a derivative thereof.

5-norbornene-endo-2,3-dicarboxylic anhydride and 5-norbornene-exo-2,3-dicarboxylic anhydride were mixed together, tetrahydrofuran was added to the resulting mixture, and a hydrogenation was conducted under a hydrogen atmosphere using 5% palladium-carbon as a catalyst. The hydrogenation rate was 100%. Following completion of the hydrogenation reaction, the product was filtered and dried. The resulting powdered mixture of norbornane-endo-2,3-dicarboxylic anhydride and norbornane-exo-2,3-dicarboxylic anhydride (exo stereoisomeric ratio for the general formula (2) type=50%) was used as the test material.

Example 16

To 10.0 g of norbornane-2,3-dicarboxylic anhydride (exo stereoisomeric ratio for the general formula (2) type=50%) were added 33.8 g of water and 16.0 g of a 30 wt % aqueous solution of sodium hydroxide (1.0 equivalents relative to the norbornane-2,3-dicarboxylic anhydride mixture), and the mixture was stirred at 70° C. for 10 minutes. The solid was then separated by filtration and dried. The obtained solid was 4.62 g (exo stereoisomeric ratio for the general formula (2) type=88%).

Example 17

With the exception of adding 48.9 g of water, preparation was conducted in the same manner as the example 16. The obtained solid was 2.42 g (exo stereoisomeric ratio for the general formula (2) type=91%).

Example 18

With the exceptions of using 41.6 g of water and 12.0 g of the 30 wt % aqueous solution of sodium hydroxide (0.75 equivalents relative to the norbornane-2,3-dicarboxylic anhydride mixture), preparation was conducted in the same manner as the example 16. The obtained solid was 1.84 g (exo stereoisomeric ratio for the general formula (2) type=88%).

Example 19

With the exceptions of using 38.8 g of water and 16.0 g of the 30 wt % aqueous solution of sodium hydroxide (1.0 equivalents relative to the norbornane-2,3-dicarboxylic anhydride mixture), preparation was conducted in the same manner as the example 16. The obtained solid was 4.01 g (exo stereoisomeric ratio for the general formula (2) type=88%).

Example 20

With the exceptions of using 33.2 g of water and 24.1 g of the 30 wt % aqueous solution of sodium hydroxide (1.5 equivalents relative to the norbornane-2,3-dicarboxylic anhydride mixture), preparation was conducted in the same manner as the example 16. The obtained solid was 6.91 g (exo stereoisomeric ratio for the general formula (2) type=83%). Furthermore, the filtrate exhibited an endo stereoisomeric ratio for the general formula (2) type=83%.

Example 21

With the exceptions of using 27.6 g of water and 32.2 g of the 30 wt % aqueous solution of sodium hydroxide (2.0 equivalents relative to the norbornane-2,3-dicarboxylic anhydride mixture), preparation was conducted in the same manner as the example 16. The obtained solid was 9.24 g (exo stereoisomeric ratio for the general formula (2) type=76%). Furthermore, the filtrate exhibited an endo stereoisomeric ratio for the general formula (2) type=90%.

Example 22

With the exceptions of using 21.6 g of water and 12.0 g of the 30 wt % aqueous solution of sodium hydroxide (0.75 equivalents relative to the norbornane-2,3-dicarboxylic anhydride mixture), preparation was conducted in the same manner as the example 16. The obtained solid was 5.39 g (exo stereoisomeric ratio for the general formula (2) type=85%). Furthermore, the filtrate exhibited an endo stereoisomeric ratio for the general formula (2) type=76%.

Example 23

With the exceptions of using 18.8 g of water and 16.1 g of the 30 wt % aqueous solution of sodium hydroxide (1.0 equivalents relative to the norbornane-2,3-dicarboxylic anhydride mixture), preparation was conducted in the same manner as the example 16. The obtained solid was 7.61 g (exo stereoisomeric ratio for the general formula (2) type 81%). Furthermore, the filtrate exhibited an endo stereoisomeric ratio for the general formula (2) type=83%.

[Examples Using Methyl-5-Norbornene-2,3-Dicarboxylic Anhydride as the Mixture]

Methyl-5-norbornene-2,3-dicarboxylic anhydride was used as the dicarboxylic acid represented by the general formula (1) or a derivative thereof.

The methylcyclopentadiene obtained by thermal decomposition of 186.29 g of methylcyclopentadiene dimer (manufactured by Avocado Research Chemicals Ltd.) was added dropwise to a mixture of 112.86 g of acetone and 175.6 g of maleic anhydride (manufactured by Wako Pure Chemical Industries Ltd.) that was cooled in an ice bath. Following reaction at temperatures up to room temperature, the solvent was removed, yielding 329.8 g of methyl-norbornene-2,3-dicarboxylic anhydride that was a cloudy white color. 320 g of this suspension was heated at 180° C. for 3 hours to effect a stereoisomerization and complete preparation of the test material.

Example 24

To 10.0 g of stereoisomerized methyl-5-norbornene-2,3-dicarboxylic anhydride were added 18.5 g of water and 16.5 g of a 30 wt % aqueous solution of sodium hydroxide (1.1 equivalents relative to the methyl-5-norbornene-2,3-dicarboxylic anhydride mixture), and the mixture was stirred at 70° C. for 15 minutes. The solid was then separated by filtration. The filtered solid was 7.4 g (exo stereoisomeric ratio for the methyl-5-norbornene-2,3-dicarboxylic acid positional isomeric mixture=88%).

Example 25

With the exception of adding 38.5 g of water, preparation was conducted in the same manner as the example 24. The filtered solid was 3.6 g (exo stereoisomeric ratio for the methyl-5-norbornene-2,3-dicarboxylic acid positional isomeric mixture=93%).

[Examples Using 5-Norbornene-2,3-Dicarboxylic Anhydride as the Mixture]

5-norbornene-2,3-dicarboxylic anhydride was used as the dicarboxylic acid represented by the general formula (1) or a derivative thereof.

Example 26

To 10.0 g of 5-norbornene-2,3-dicarboxylic anhydride (exo stereoisomeric ratio for the general formula (1) type ~48%) were added 48.9 g of water and 1.6 g of a 30 wt % aqueous solution of sodium hydroxide (0.1 equivalents relative to the 5-norbornene-2,3-dicarboxylic anhydride, 0.19 equivalents relative to 5-norbornene-endo-2,3-dicarboxylic anhydride), and the mixture was stirred at 70° C. for 10 minutes. The solid was then separated by filtration and dried. The obtained solid was 4.47 g (exo stereoisomeric ratio for the general formula (1) type=50%).

Example 27

To 10.0 g of 5-norbornene-2,3-dicarboxylic anhydride (exo stereoisomeric ratio for the general formula (1) type=48%) were added 3.3 g of water and 87 g of a 45 wt % aqueous solution of sodium hydroxide (8.1 equivalents relative to the 5-norbornene-2,3-dicarboxylic anhydride, 15.6 equivalents relative to 5-norbornene-endo-2,3-dicarboxylic anhydride), and the mixture was stirred at 70° C. for 10 minutes. The solid was then separated by filtration and dried. The obtained solid was 15.0 g (exo stereoisomeric ratio for the general formula (1) type=51%).

Example 28

To 10.0 g of 5-norbornene-2,3-dicarboxylic anhydride (exo stereoisomeric ratio for the general formula (1) type=48%) was added 8.6 g of a 30 wt % aqueous solution of sodium hydroxide (0.5 equivalents relative to the 5-norbornene-2,3-dicarboxylic anhydride, 1.0 equivalents relative to 5-norbornene-endo-2,3-dicarboxylic anhydride), and the mixture was stirred at 70° C. for 10 minutes. The solid was then separated by filtration and dried. The obtained solid was 11.8 g (exo stereoisomeric ratio for the general formula (1) type=52%).

Example 29

To 10.0 g of 5-norbornene-2,3-dicarboxylic anhydride (exo stereoisomeric ratio for the general formula (1) type=48%) were added 3.8 g of water and 66 g of a 30 wt % aqueous solution of sodium hydroxide (4.1 equivalents relative to the 5-norbornene-2,3-dicarboxylic anhydride, 7.9 equivalents relative to 5-norbornene-endo-2,3-dicarboxylic anhydride), and the mixture was stirred at 70° C. for 10 minutes. The solid was then separated by filtration and dried. The obtained solid was 14.8 g (exo stereoisomeric ratio for the general formula (1) type=55%).

Example 30

To 10.0 g of the disodium 5-norbornene-2,3-dicarboxylate obtained in the example 2 (exo stereoisomeric ratio for the general formula (1) type=84%) were added 39.3 g of water and 10.7 g of a 30 wt % aqueous solution of hydrogen chloride (2 equivalents relative to the sodium 5-norbornene-2,3-dicarboxylate), and the mixture was stirred at 70° C. for 10 minutes to effect dissolution. The solution was then left to stand for 3 hours at 5° C., which lead to the precipitation of crystals, and the solid was separated by filtration, washed with 30 g of water, and the solid was once again separated and dried. The obtained solid was 8.80 g.

To the thus obtained solid was added 24.5 g of acetic anhydride (5 equivalents relative to 5-norbornene-2,3-dicarboxylic acid), and the mixture was stirred at 70° C. for 10 minutes to effect dissolution. The solution was then left to stand for 3 hours at 5° C., which lead to the precipitation of crystals, and the solid was separated by filtration, washed with 30 g of water, and the solid was once again separated and dried, yielding 5-norbornene-2,3-dicarboxylic anhydride. The obtained solid was 5.20 g (exo stereoisomeric ratio for the general formula (1) type=85%).

[Examples Using 5-Norbornene-2,3-Dicarboxylic Anhydride and Methyl-5-Norbornene-2,3-Dicarboxylic Anhydride as the Mixture]

5-norbornene-2,3-dicarboxylic anhydride and methyl-5-norbornene-2,3-dicarboxylic anhydride were used as the dicarboxylic acid represented by the general formula (1) or a derivative thereof.

Example 31

To 5.0 g of stereoisomerized methyl-5-norbornene-2,3-dicarboxylic anhydride (exo stereoisomeric ratio for the general formula (1) type=48%) and 5.0 g of 5-norbornene-2,3-dicarboxylic anhydride (exo stereoisomeric ratio for the general formula (1) type=48%) were added 18.5 g of water and 16.5 g of a 30 wt % aqueous solution of sodium hydroxide (1.1 equivalents relative to 5-norbornene-2,3-dicarboxylic anhydride), and the mixture was stirred at 70° C. for 10 minutes. The solid was then separated by filtration and dried. The obtained solid was 7.4 g (exo stereoisomeric ratio for the general formula (1) type=87%).

Comparative Example 1

25 mL of acetone was added to 20.0 g of 5-norbornene-1,4-dicarboxylic anhydride (exo stereoisomeric ratio for the general formula (1) type=22%) and a recrystallization was attempted. No crystals were obtained.

Comparative Example 2

With the exception of using 20 mL of acetone, the procedure of the comparative example 1 was repeated. The obtained solid was 1.21 g (exo stereoisomeric ratio for the general formula (1) type=4.6%)

Comparative Example 3

With the exception of using 15 mL of acetone, the procedure of the comparative example 1 was repeated. The obtained solid was 4.50 g (exo stereoisomeric ratio for the general formula (1) type=13%)

INDUSTRIAL APPLICABILITY

According to a separation method of the present invention, stereoisomers of a dicarboxylic acid having a norbornene or norbornane structure, or a derivative thereof can be separated simply and efficiently. The exo isomer or endo isomer of the dicarboxylic acid having a norbornene or norbornane structure or a derivative thereof obtained using the separation method of the present invention can be used favorably as the raw material for agricultural chemicals or electronic materials.

What is claimed is:

1. A method of separating an endo isomer and an exo isomer of a dicarboxylic acid represented by formula (1),

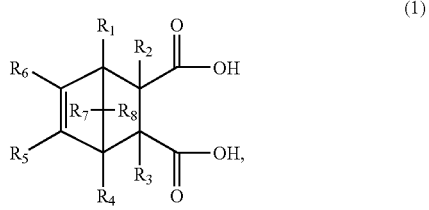

wherein, $R_1$ to $R_8$ represent a hydrogen atom, methyl group, ethyl group, or butyl group, or an anhydride thereof, or formula (2),

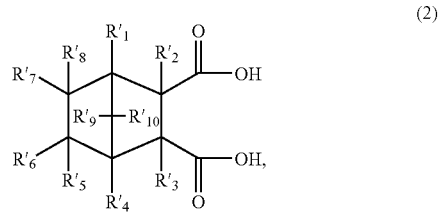

wherein, $R'_1$ to $R'_{10}$ represent a hydrogen atom, methyl group, ethyl group, or butyl group, or an anhydride thereof, the method comprising the steps of:
 (a) providing a mixture comprising mainly the endo isomer of the dicarboxylic acid represented by formula (1) or (2) or an anhydride thereof, and the exo isomer of the dicarboxylic acid represented by formula (1) or (2) or an anhydride thereof;
 (b) mixing the mixture with an alkali metal hydroxide and a solvent; and
 (c) filtering the mixture obtained in step (b) to separate an aqueous phase and a solid phase, thereby separating the endo isomer from the exo isomer.

2. The method of separating an endo isomer and an exo isomer according to claim 1, wherein said dicarboxylic acid consists essentially of a dicarboxylic acid represented by the formula (1) or an anhydride thereof.

3. The method of separating an endo isomer and an exo isomer according to claim 2, wherein the alkali metal hydroxide is used in a quantity that achieves at least 0.2 equivalents relative to the endo isomer, and no more than 8 equivalents relative to the mixture.

4. The method of separating an endo isomer and an exo isomer according to claim 2, wherein the solvent is used in a quantity of at least 0.7 g relative to 6 mmol of the mixture, and no more than the larger of either 10 g relative to 6 mmol of the mixture or 20 g relative to 6 mmol of the endo isomer.

5. The method of separating an endo isomer and an exo isomer according to claim 2, wherein the dicarboxylic acid represented by formula (1) or an anhydride thereof is 5-norbornene-2,3-dicarboxylic acid or an anhydride thereof.

6. The method of separating an endo isomer and an exo isomer according to claim 1, wherein said dicarboxylic acid consists essentially of a carboxylic acid represented by formula (2) or an anhydride thereof.

7. The method of separating an endo isomer and an exo isomer according to claim 6, wherein the alkali metal hydroxide is used in a quantity that achieves at least 0.35 equivalents and no more than 8 equivalents relative to the mixture.

8. The method of separating an endo isomer and an exo isomer according to either claim 6, wherein the solvent is used in a quantity of at least 0.7 g relative to 6 mmol of the mixture, and no more than 20 g relative to 6 mmol of the mixture.

9. The method of separating an endo isomer and an exo isomer according to claim 6, wherein the dicarboxylic acid represented by formula (2) or an anhydride thereof is norbornane-2,3-dicarboxylic acid or an anhydride thereof.

10. A method of separating an endo isomer and an exo isomer of a salt of a dicarboxylic acid represented by formula (1),

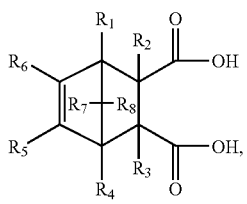
(1)

wherein, $R_1$ to $R_8$ represent a hydrogen atom, methyl group, ethyl group, or butyl group, or formula (2),

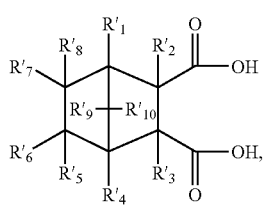
(2)

wherein, $R'_1$ to $R'_{10}$ represent a hydrogen atom, methyl group, ethyl group, or butyl group, the method comprising the steps of:

(a) providing a mixture comprising mainly the endo isomer of the salt of the dicarboxylic acid represented by formula (1) or (2), and the exo isomer of the salt of the dicarboxylic acid represented by formula (1) or (2);

(b) mixing the mixture with a solvent; and (c) filtering the mixture obtained in step (b) to separate an aqueous phase and a solid phase, thereby separating the endo isomer from the exo isomer.

11. The method of separating an endo isomer and an exo isomer according to claim 10, wherein said salt of a dicarboxylic acid consists essentially of a salt of a dicarboxylic acid represented by formula (1).

12. The method of separating an endo isomer and an exo isomer according to claim 11, wherein the salt of the dicarboxylic acid represented by formula (1) is a salt of 5-norbornene-2,3-dicarboxylic acid.

13. The method of separating an endo isomer and an exo isomer according to claim 10, wherein said salt of a dicarboxylic acid consists essentially of a salt of a dicarboxylic acid represented by formula (2), with a solvent.

14. The method of separating an endo isomer and an exo isomer according to claim 13, wherein the salt of the dicarboxylic acid represented by formula (2) is a salt of norbornane-2,3-dicarboxylic acid.

15. The method of separating an endo isomer and an exo isomer according to claim 1, wherein step (c) is a step of filtering a mixture obtained from the mixing step, and either obtaining an endo isomer of a salt of the dicarboxylic acid represented by formula (1) or (2) as a liquid phase, or obtaining an exo isomer of a salt of the dicarboxylic acid represented by formula (1) or (2) as a solid phase.

16. The method of separating an endo isomer and an exo isomer according to claim 15, further comprising the step of obtaining an endo isomer or an exo isomer of the dicarboxylic acid represented by formula (1) or (2), from the endo isomer or the exo isomer of the salt of the dicarboxylic acid represented by the formula (1) or (2).

17. The method of separating an endo isomer and an exo isomer according to claim 15, further comprising the step of obtaining an endo isomer or an exo isomer of an anhydride of the dicarboxylic acid represented by formula (1) or (2) from the endo isomer or the exo isomer of the dicarboxylic acid represented by formula (1) or (2) or a salt thereof.

* * * * *